United States Patent [19]
Prat

[11] Patent Number: 4,582,076
[45] Date of Patent: Apr. 15, 1986

[54] APPARATUS FOR CLEANING AND STERILIZING SOFT CONTACT LENSES

[76] Inventor: Jacques E. Prat, Bégadan 33340, Lesparre Médoc, France

[21] Appl. No.: 602,512

[22] Filed: Apr. 20, 1984

[30] Foreign Application Priority Data

Apr. 21, 1983 [FR] France .............................. 83 06547

[51] Int. Cl.⁴ ............................................. A61L 2/18
[52] U.S. Cl. .................................. 134/57 R; 134/95; 134/107; 134/113; 134/158; 134/162; 422/300; 422/307
[58] Field of Search ................. 422/300, 301, 307, 38, 422/116; 134/56 R, 57 R, 59, 95, 105, 107, 113, 140, 143, 157, 158, 159, 162

[56] References Cited

U.S. PATENT DOCUMENTS

| | | | |
|---|---|---|---|
| 1,275,676 | 8/1918 | Halverson et al. | 422/300 X |
| 2,634,735 | 4/1953 | Buck | 134/157 X |
| 4,077,416 | 3/1978 | Johnson, Jr. et al. | 134/159 |
| 4,165,359 | 8/1979 | Thomas et al. | 422/300 X |
| 4,235,842 | 11/1980 | Thomas et al. | 422/307 X |
| 4,369,355 | 1/1983 | Helixon | 422/301 X |
| 4,376,096 | 3/1983 | Bonen | 422/307 X |

FOREIGN PATENT DOCUMENTS 2259618 8/1975 France .

*Primary Examiner*—Philip R. Coe
*Attorney, Agent, or Firm*—Charles E. Brown; Charles A. Brown

[57] ABSTRACT

An apparatus for cleaning and sterilizing soft contact lenses comprises a disinfection unit and a control unit. The disinfection unit comprises a receptacle for selectively containing a cleaning liquid and a sterilizing liquid, and a lens holder having perforate lens compartments. The lens holder is removably mounted in the receptacle and rotatable therein. The rotation of the lens holder effects enhanced cleansing action by turbulent flow of the cleaning liquid over the lenses. A heater is preferably mounted on the control unit in intimate heat transfer relation with the disinfection unit when the units are secured together (e.g. with permanent magnets) for heating the sterilizing liquid in the receptacle. The control unit controls the heater for providing alternating high temperature periods (not greater than about 60° C.) and lower temperature periods for sterilizing the cleaned lenses.

20 Claims, 6 Drawing Figures

U.S. Patent    Apr. 15, 1986    4,582,076
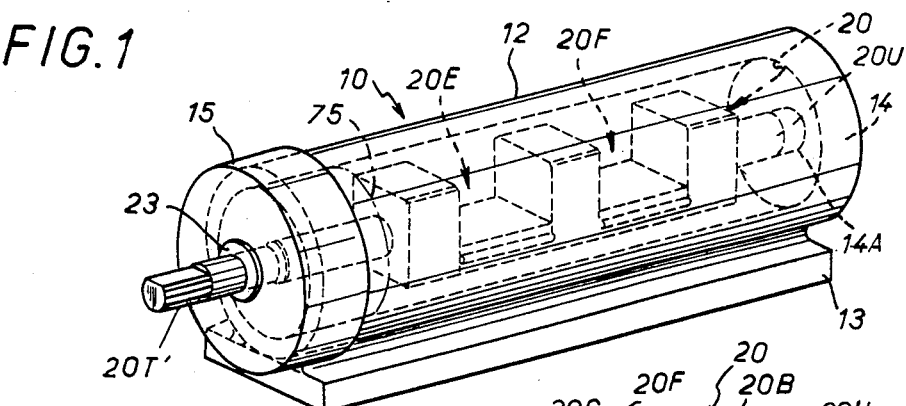
FIG.1
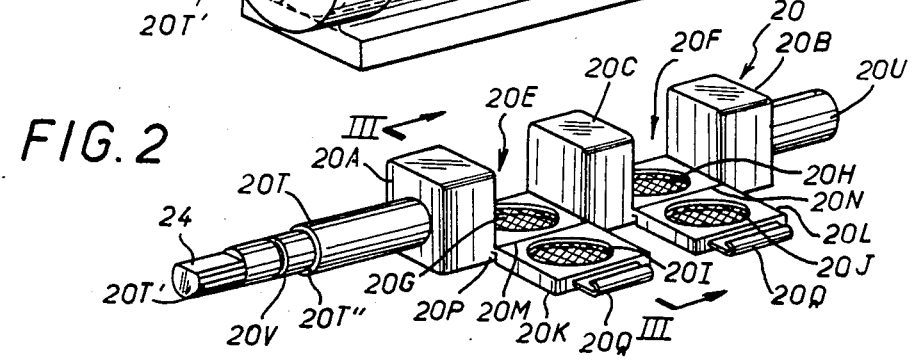
FIG.2
FIG.3                    FIG.4
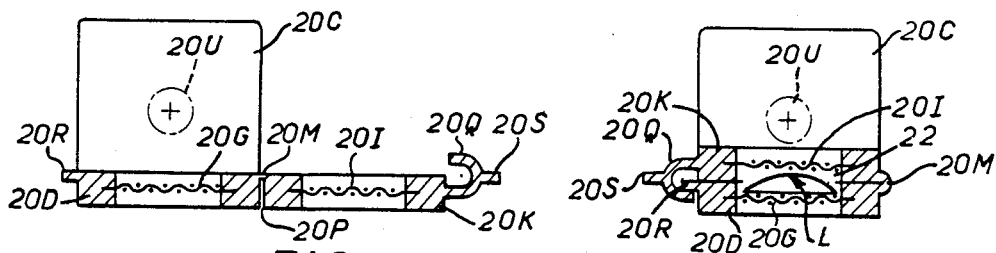
FIG.5                    FIG.6
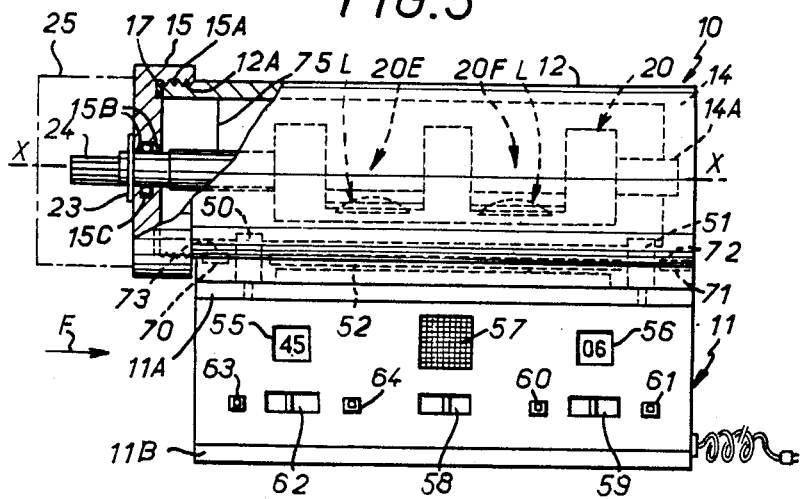
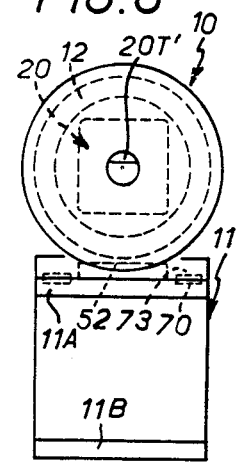

APPARATUS FOR CLEANING AND STERILIZING SOFT CONTACT LENSES

BACKGROUND OF THE INVENTION

The present invention relates generally to hydrophilic, soft contact lenses and more particularly to the care and maintenance thereof by cleaning and sterilization.

It is known that soft contact lenses must be cleaned and sterilized daily.

To date, after removal by the wearer hydrophilic, soft contact lenses are first cleaned and then sterilized. Commonly such soft contact lenses are cleaned with an appropriate solution, rubbing both sides and rinsing with a physiological serum or other similar solution. These steps are carried out by hand which requires the user's undivided attention, with nevertheless the attendant risk of damaging the lenses by scratching, breaking or tearing particularly since there is a tendency to prescribe thinner and more fragile contact lenses. Further, risks of contamination must be minimized which means perfectly clean hands and nails before each disinfecting operation.

This procedure is therefore tedious for the user who must carry it out day after day and relatively expensive owing to the cost of the special cleaning and rinsing solutions.

After cleaning the lenses they must be "cold" sterilized with chemical solutions at ambient temperature or "hot" sterilized in a special sterilization unit.

PRIOR ART

In French Pat. No. 74 04041 (publication No. 2,259,618) there is provided a "hot" aseptor comprising a cell into which two electrodes protrude and inside which a tube containing soft contact lenses and a suitable liquid may be received. In such an aseptor sterilization is effected by boiling a liquid, there water, introduced into the cell and heated by the electrodes. Sterilization of the lenses is completed when the liquid has entirely evaporated.

According to French Pat. No. 76 33671 (publication No. 2,369,847) each of the lenses is placed in a recess formed in a cover closing off a cell, each of the recesses receiving a liquid such as a physiological serum and a liquid adapted to be brought to a boil by an electrode is poured into the cell whereby when the liquid in the cell the lenses has evaporated lenses are sterilized.

According to another hot sterilization procedure taught by French Pat. No. 76 20984 (publication No. 2,317,942) the lenses are sterilized by not dry air by means of a heating element which gives off heat previously stored during a predetermined period of time, the hot air acts on a contact lens holder immersed in a bath of a suitable solution.

Hot sterilizations briefly described above, are not devoid of drawbacks since the temperature of sterilization is either not controlled at all or randomly controlled. But since sterilization must be carried out daily it may have a detrimental effect on the original properties of the lenses causing, e.g., opaqueness or yellowing. Further, it has been found that despite daily sterilization such contact lenses must periodically be cleaned professionally.

Thus, as we have been present-day cleaning and sterilization of hydrophilic, soft contact lenses do not give complete satisfaction.

OBJECT AND SUMMARY OF THE INVENTION

An object of the present invention is to provide easier and more effective cleaning of soft contact lenses while reducing the likelihood of damage thereto. To this end there is provided a novel apparatus for cleaning and sterilizing contact lenses which is of simple construction and is convenient to use and reduces the likelihood of damage to the contact lenses through handling and "aging" through sterilization.

According to the invention there is provided apparatus for cleaning and hot sterilizing hydrophilic, soft contact lenses comprising a first, disinfection unit including a receptacle selectively adapted to be at least partly filled with a disinfecting liquid, that is, selectively a cleaning liquid and sterilizing liquid. A lens holder accommodates two or more contact lenses. Means removably mounts the lens holder inside the receptatacle. Communication is provided between the disinfecting liquid inside the receptacle and lenses accommodated in the lens holder. The lens holder is rotatably mounted in the receptacle and is rotated in the receptacle for effecting enhanced cleansing action by turbulent flow of the disinfecting liquid over the lens. Means is provided for heating the disinfecting liquid inside the receptacle for hot sterilization of the contact lenses after cleaning. A second, control unit controls the means for heating the disinfecting liquid to provide a series of alternating high temperature (not greater than about 60°) and lower temperature periods.

The lens holder advantageously comprises two axially spaced and radially offset lens compartments with respect to the axis rotation of the lens holder.

According to another preferred feature of the invention the first and second units are detachably secured together by means of at least one permanent magnet affixed to one of the units and a magnetisable element affixed to the other of the units cooperable with the permanent magnet.

The sterilizer according to the invention has various advantages over the prior art as regard both cleaning and the sterilization.

One of the main advantages resides in the fact that the handling of the lens is practically eliminated. Indeed after placing the lenses on the lens holder unit the user does not have to handle the lenses other than removing them from the lens holder after sterilization.

Another advantage resides in the fact that the sterilization is preferably in accordance with the Tyndall method comprising a plurality of heating periods at a given temperature followed by cooling periods. The Tyndall method provides flawless sterilization of the contact lenses without exerting any deleterious stresses capable of adversely affecting the properties of the lenses owing in particular to the low sterilization temperature (of the order of a maximum of 60° C.). This increases the service life of the contact lenses cleaned and sterilized according to the invention and substantially facilitates the care and maintenance of soft contact lenses.

Since as noted above the disinfection unit enables satisfactory cleaning of contact lenses substantially without any handling and the control unit is adapted to ensure satisfactory sterilization according to the Tyndall method, the chance of damaging (e.g. by tearing, scratching or breaking) or contaminating soft contact lenses being cleaned or modification of the properties of the lenses (e.g., by opaqueness or yellowing) is substantially eliminated.

One more advantage of the apparatus according to the invention resides in the compactness of the disinfection unit and the control unit which are readily portable.

These and other features and advantages of the invention will become apparent from the following description, given by way of example, with reference to the accompanying drawings.

BRIEF DESCRIPTION OF THE DRAWINGS

FIG. 1 is a perspective view of a first, disinfection unit of the lens cleaning and sterilizing apparatus embodying the invention;

FIG. 2 is a perspective view of the lens holder of the disinfection unit, taken on its own, with the lens compartments open and empty;

FIG. 3 is a larger scale cross-sectional view of one of the lens compartments in its open position, taken along line III—III in FIG. 2;

FIG. 4 is a view similar to that of FIG. 3 illustrating one of the lens compartments, with a lens, in its closed position;

FIG. 5 is an elevational view of the disinfection unit associated with the control unit of the lens cleaning and sterilizing apparatus; and FIG. 6 is an end view taken in the direction of arrow F in FIG. 5.

DESCRIPTION OF THE PREFERRED EMBODIMENT

According to the preferred embodiment of FIGS. 1-6 the lens cleaning and sterilizing apparatus according to the invention comprises a first, disinfection unit generally designated by reference 10 and a second, control unit generally designated by reference 11. The disinfection unit 10 and the control unit 11 are adapted to be detachably secured together by means which are described below.

The first, disinfection unit 10 comprises a receptacle or generally cylindrical housing 12 having a flat base 13. The housing 12 is hollow. One end of the housing 12 is closed off by a fixed flat endwall 14 and the other end by a removal plug 15. The plug 15 may be fitted at the end of the housing 12 and have a seal for improving the fluidtightness. Preferably, as illustrated, the plug 15 comprises an internal screw thread 15A for threadedly engaging a screw thread 12A formed at the corresponding end of the housing 12 and an annular seal 17 is accommodated at the inner end of the plug for sealing engagement with the edge of the threaded end of the housing for ensuring fluidtightness.

The plug 15 and the endwall 14 of the cylindrical housing 12 define bearings for the lens holder or support identified generally by reference 20 in FIG. 2. The lens holder 20 is advantageously of one-piece molded plastic construction and comprises a central transverse spacer 20C and two side transverse spacers 20A and 20B respectively longitudinally spaced to opposite sides of the central transverse spacer 20C. The spacers 20A, 20B and 20C are joined together by a longitudinal wall 20D to define two compartments 20E and 20F between the central spacer 20C and the respective transverse spacers 20A and 20B. The longitudinal wall 20D defines the bottoms of the compartments 20E and 20F each having a preferably circular perforate central area 20G, 20H. Associated covers 20K and 20L for the respective compartments 20E and 20F also having perforably circular perforate central areas 20I, 20J are adapted to be superposed on the compartment bottoms defined in longitudinal wall 20D with the perforate central areas 20I, 20J and 20G, 20H in registry when the lens compartments 20E and 20F are closed. Preferably, covers 20K, 20L are integrally molded with the rest of the lens holder 20 and are hinged to the longitudinal wall 20D by straps 20M, 20N with a gap 20P formed between each of the covers 20K, 20L and the respective portion of the longitudinal wall 20D immediately below the strap 20M, 20N. The free longitudinal edge of each of the covers 20K, 20L comprises a latch 20Q adapted to cooperate with a lip or catch 20R on the edge of the longitudinal wall 20D remote from the covers 20K, 20L. A tab 20S protrudes from each latch 20Q for facilitating the grasping thereof.

The compartments 20E and 20F may therefore have an open position as illustrated in FIG. 2 for inserting and removing contact lenses or a closed position as shown in FIG. 4 in which the cover 20K, 20L is superposed on the corresponding portion of longitudinal wall 20D with the respective perforate central areas 20I and 20G and 20J and 20H in registry and a contact lenses L accommodated therebetween. The contact lenses L are preferably substantially unrestrained in their lens compartments 20E, 20F.

Extending axially outwardly from each of the side 20A, 20B of the lens holder 20 is a cylindrical shaft member 20T, 20U of which the shaft member 20T is the longer and advantageously comprises a splined portion 20T' and a flat 24 whose function will be brought out below. Shaft member 20U is adapted to be received in bearing 14A in endwall 14 and shaft member 20T protrudes through bearing 15D defined by plug 15. Shaft member 20T has a terminal portion which extends beyond plug 15, a shoulder 20T" limits the axial play of the lens holder 20 inside the housing 12. A toroidal seal 15C received in an annular recess in the endwall of the plug 15 provides fluidtightness. Plug 15 is advantageously secured to the lens holder 20 by an annular groove 20V in shaft 20T cooperating with a circlip 23. The lens holder 20 is thus secured relative to the plug 15 while admitting of slight relative axial play.

Lens holder 20 received in housing 12 is mounted for rotation about axis X—X. The compartments 20E and 20F and therefore the lenses accommodated therein are radially offset relative to the axis X—X so that the circumferential movement of the lenses L in their compartments 20E and 20F about axis X—X produces a turbulent, cleansing action with the liquid with which the housing 12 is previously filled.

The disinfection unit 10 has at least one and preferably two temperature sensors 50, 51 protruding inside the housing 12 and having electrical prongs protruding beyond the lower side of the base 13 of the housing 12. The base 13 is also designed to accommodate a resistance heater mounted on the control unit 11.

The control unit 11 comprises a generally rectangular block having a top 11A and a bottom 11B and control means on a front wall for controlling the resistance heater.

In the illustrated embodiment the resistance heater comprises a plate 52 overlying the top 11A of the control unit 11 and the control means comprising a temperature sensor 55, a timer 56 and sound alarm or warning device 57 together with an on-off switch 58 is mounted in the front face of the control unit 11. A switch 59 is provided for "fast" and "moderate" sterilization with corresponding indicator lamps 60 and 61. Another switch 62 with a corresponding indicator lamp 63 may be provided for controlling optional micro motor drive means 25 (in phantom line in FIG. 5) for rotating the lens holder 20. At 64 is a cutoff switch for the sound alarm or warning device 57.

As mentioned above the disinfection unit 10 and the control unit 11 are adapted to be detachably secured together by permanent magnet means. In the illustrated embodiment two permanent magnets 70 and 71 are disposed proximate to the respective ends of the control unit 11 for cooperation with corresponding magnetizable elements 72 and 73 carried by the disinfection unit 11 so that the disinfection and control units may be rapidly and readily connected and disconnected without any tools whatever.

The control unit 11 is equipped with all the necessary means for carrying out the Tyndall sterilization method including a plurality of heating periods alternating with a plurality of cooling periods. The temperature and the duration of each of the periods are controlled by the control unit 11. It is noted that the provision of temperature sensors 50 and 51 in the detection unit 10 enables precision readings to be obtained.

In the disinfection unit 10 there is provided a liquid level line or indicator, schematically shown at 75 in FIGS. 1 and 5, proximate to the end of the housing 12 adjacent the plug 15.

The cleaning and sterilization of contact lenses are carried out in accordance with the following steps. First, the contact lenses are placed in the perforate central areas 20G and 20H of the respective compartments 20E and 20F and the covers 20K and 20L are latched closed as illustrated in FIG. 4. To avoid any error indicia are provided for the respective compartments 20E and 20F designating the left and right contact lens respectively, for example the words "left" and "right" are inscribed on the outer faces of the respective covers 20K and 20L.

The housing 12 is then stood on its endwall 14 and filled with a liquid, for example, a 3% hydrogen peroxide solution, to the level of line 75.

The lens holder 20 with lenses L is then lowered into the housing 12 and the plug 12 is then tightened on the housing 12. The lenses L are then cleaned by rotating the shaft 20T manually or mechanically (by micro motor 25) in one direction or alternately clockwise and counterclockwise. The cleansing of the lenses L is effected by the turbulent flow of the solution through the perforate compartments 20E and 20F housing lenses L. By way of nonlimiting example the duration of cleaning operation per se may last between about two and six minutes the control means providing a blip after after two and four minutes and a continuous sound signal after six minutes. The sound signal reminds the user that prolonged immersion of the lenses in the hydrogen peroxide solution should be eschewed.

Thereafter the disinfection unit is opened and emptied and refilled with a rinsing solution such as physiological serum and then closed again. The lens holder or support 20 is then rotated manually or mechanically for a period of the order of two minutes and then the rinsing solution is poured out.

After cleaning and rinsing the lenses L they may be sterilized hot. The disinfection unit 10 is again filled with an appropriate physiological serum and then the disinfection unit 10 is connected to the control unit 11, taking care to orient the flat 24 on shaft 20T facing upwardly so that the compartments 22 accommodating lenses L are in the lower part of the housing 12 and immersed in the physiological serum. The desired sterilizing cycle is selected on the control unit according to the Tyndall method. It is noted that the sterilization may either be fast or moderate. A moderate sterilization is carried out at lower temperatures and has the advantage of avoiding any deleterious stressing of the lenses L which in time may affect the properties of the lenses. Nevertheless the control unit may provide fast sterilizing program which from the point of view of sterilization per se is entirely satisfactory, and of course faster than the moderate program.

After hot sterilization the user is warned by the sound alarm 57.

It will be noted that the handling of the soft contact lenses for cleaning and sterilization is reduced to placing them into their compartments before cleaning and removing them from their compartments after sterilization thereby substantially reducing the likelihood of scratching, breaking or otherwise damaging the lenses.

The control unit 11 is adapted to be supplied through a normal electrical lead and connected to electric mains supply, or a separate electric source such as normal batteries or rechargeable batteries.

Finally the present invention is not intended to be limited to the illustrated and described embodiment but admits of all alternatives and modification understood to those skilled in the art without departing from the scope of the appended claims.

What I claim is:

1. Apparatus for cleaning and hot sterilizing hydrophilic, soft contact lenses comprising a first, disinfection unit including a receptacle adapted to be at least partly filled with a disinfecting liquid, a lens holder for accommodating two contact lenses, means for removably mounting said lens holder inside said receptacle, means for providing communication between liquid in said receptable and lenses accommodated in said lens holder, means for rotatably mounting said lens holder in said receptacle, means for rotating said lens holder in said receptacle for effecting cleansing action by turbulent flow of the disinfecting liquid over the lenses, means for heating the disinfecting liquid inside receptacle for hot sterilizing the lenses after cleaning, and a second, control unit for controlling said means for heating the disinfecting liquid for providing a series of alternating high temperature (not greater than about 60° C.) and low temperature periods.

2. Apparatus according to claim 1, wherein said receptacle is selectively adapted to be at least partly filled with and emptied of a rinsing liquid.

3. Apparatus according to claim 2, wherein said lens holder comprises two compartments for accommodating the respective lens, said lens compartments being disposed radially offset relative to the axis about which said lens holder is adapted to be rotated for enhancing the cleansing action between the cleaning liquid on the lenses in said compartments.

4. Apparatus according to claim 3, wherein said means for rotatably mounting said lens holder comprises bearing means, said lens holder having a shaft member journaled in said bearing means.

5. Apparatus according to claim 4, wherein said compartments are longitudinally spaced along said lens holder.

6. Apparatus according to claim 3, wherein said compartments each comprise a bottom and a cover hinged relative to said bottom, said means providing communication between liquid in said receptacle and lenses accommodated in said lens holder comprising perforations in said bottoms and said covers for effecting the cleansing action.

7. Apparatus according to claim 3, wherein said lens holder comprises a shaft member at each end, said means for rotatably mounting said lens holder comprising a bearing in an endwall of said receptacle and another bearing in a removable plug adapted to be received in the other end of said receptacle.

8. Apparatus according to claim 7, wherein said plug and other end of said receptacle are complementarily threaded for threaded engagement.

9. Apparatus according to claim 3, wherein said lens holder is of one-piece molded plastic construction comprising shaft members at each end, a transverse spacer between each shaft member and an adjacent ones of said compartments, and another transverse spacer between said compartments.

10. Apparatus according to claim 3, wherein said lens holder is of one-piece molded plastic construction comprising shaft members at each end, a transverse spacer between each shaft member and an adjacent ones of said compartments, another transverse spacer between said compartments, each of said compartments having a bottom and a cover hinged to its respective bottom, the bottoms of said compartments interconnect said spacers, and the hinged cover of each of said compartments is adapted to be pivoted from an open position generally in the same plane as its associated bottom and a closed position overlying the associated bottom and extending between adjacent ones of said spacers.

11. Apparatus according to claim 1, wherein the disinfecting liquid selectively comprises a cleaning liquid and a sterilizing liquid for respectively cleaning and sterilizing the lenses.

12. Apparatus according to claim 1, wherein said means for heating is mounted in said control unit and arranged to be in direct heat transfer relation with said desinfection unit.

13. Apparatus according to claim 12, and means for releasably securing said disinfection unit and said control unit together.

14. Apparatus according to claim 13, wherein said disinfection unit comprises at least one temperature sensor adapted to be connected to control means of said control unit when said disinfection unit and said control unit are in operative engagement.

15. Apparatus according to claim 13, wherein said means for releasably securing said disinfection unit and said control unit together comprise a permanent magnet affixed to one of said units and magnetizable material affixed to the other of said units.

16. Apparatus according to claim 12, wherein said receptacle has a base, said base being shaped to receive the configuration of said means for heating protruding from an adjacent portion of said control unit when said disinfection unit and said control are in operative engagement.

17. Apparatus according to claim 1, wherein said means for rotating said lens holder has means for determining the correct position of said compartments relative to said control unit for sterilizing lens in said compartments.

18. Apparatus according to claim 1, wherein said receptacle has an endwall adapted to support said receptacle for filling the same and a base for supporting said receptable in its operative position.

19. Apparatus according to claim 1, wherein said means for rotating said lens holder comprises a micro motor, said micro motor being selectively operative for continuous and alternating operation.

20. Apparatus according to claim 1, wherein said control unit comprises control means including an on-off switch, a sound alarm, a timer, a temperature sensing means, a control switch for fast or moderate sterilization, and switch means for controlling said means for rotating said lens holder.

* * * * *